(12) United States Patent
Colgin et al.

(10) Patent No.: US 8,518,881 B2
(45) Date of Patent: Aug. 27, 2013

(54) METHODS FOR INDUCING SUPEROVULATION IN UNGULATES

(75) Inventors: Mark A. Colgin, Castle Rock, CO (US); Richard G. Donnelly, Fort Collins, CO (US); Brad Stroud, Weatherford, TX (US)

(73) Assignee: AspenBio Pharma, Inc., Castle Rock, CO (US)

( * ) Notice: Subject to any disclaimer, the term of this patent is extended or adjusted under 35 U.S.C. 154(b) by 241 days.

(21) Appl. No.: 12/028,155

(22) Filed: Feb. 8, 2008

(65) Prior Publication Data

US 2008/0312151 A1 Dec. 18, 2008

Related U.S. Application Data

(60) Provisional application No. 60/888,807, filed on Feb. 8, 2007.

(51) Int. Cl.
*A61K 38/24* (2006.01)
*C07K 14/59* (2006.01)

(52) U.S. Cl.
USPC ............. 514/9.9; 514/9.8; 530/350; 530/397; 530/398

(58) Field of Classification Search
None
See application file for complete search history.

(56) References Cited

U.S. PATENT DOCUMENTS

| | | | |
|---|---|---|---|
| 4,780,451 A | 10/1988 | Donaldson | |
| 5,162,306 A * | 11/1992 | Donaldson | 514/12 |
| 5,589,457 A | 12/1996 | Wiltbank et al. | |
| 5,792,785 A | 8/1998 | Sharp et al. | |
| 6,403,631 B1 | 6/2002 | Sharp et al. | |
| 7,202,215 B2 * | 4/2007 | Lustbader | 514/13 |

FOREIGN PATENT DOCUMENTS

| | | | |
|---|---|---|---|
| EP | 404458 | * | 6/1990 |
| EP | 1 188 444 | | 3/2002 |
| WO | WO 03/064677 | | 8/2003 |

OTHER PUBLICATIONS

Website downloaded Apr. 6, 2012 from sykes.net.au/sykes/plusetfaq. htm#•_How_is_biological_activity_measured; 4 pages total.*
Lucy, M.C. (2001) "Reproductive loss in high-producing dairy cattle: Where will it end?," *J. Dairy Sci.*, 84:1277-1293.
Roche et al. (2000) "Reproductive management of postpartum cows," *Anim. Reprod. Sci.*, 60-61:703-712.
Royal et al. (2000) "Declining fertility in dairy cattle: changes in traditional and endocrine parameters of fertility," *Anim. Sci.*, 70:487-502.
Chagas e Silva et al. (2002) "Plasma progesterone profiles and factors affecting embryo-fetal mortality following embryo transfer in dairy cattle" *Theriogenology* 58(1):51-59 (Abstract only).
D'Occhio et al. (2000) "reproductive responses of cattle to GnRH agonists" *Anim. Reprod. Sci.* 60-61:433-442.
De Rensis et al. (2002) "Fertility in postpartum dairy cows in winter or summer following estrus synchronization and fixed time AI after the induction of a LH surge with GnRH or hCG"; *Theriogenology* 58(9):1675-1687 (Abstract only).
Farin et al. (1988) "Effect of Luteinizing Hormone and Human Chorionic Gonadotropin on Cell Populations in the Ovine Corpus Luteum"; *Biol. Reprod.* 38:413-421.
Gustafsson, H. and K. Larsson (1985) "Embryonic mortality in heifers after artificial insemination and embryo transfer: differences between virgin and repeat breeder heifers," *Res. Vet. Sci.*, 39:271-274.
Hoyer and Niswender (1985) "The regulation of steroidogenesis is different in the two types of ovine luteal cells"; *Can. J. Physiol. Pharmacol.* 63(3):240-248 (Abstract only).
Lee et al. (1983) "Efficacy of gonadotropin-releasing hormone administered at the time of artificial insemination of heifers and postpartum and repeat breeder dairy cows"; *Am. J. Vet. Res.* 44(11):2160-2163 (Abstract only).
Macmillan et al. (1996) "The effects of lactation on the fertility of dairy cows" *Aust. Vet. J.*, 73:141-147.
Martinez et al. (1999) "Effect of LH or GnRH on the dominant follicle of the first follicular wave in beef heifers"; *Anim. Reprod. Sci.* 57:23-33.
Pierce JG, Parsons (1981) "Glycoprotein hormones: structure and function," *Ann.Rev.Biochem.* 50:465-495.
Pursley et al. (1998) "Effect of time of artificial insemination on pregnancy rates, calving rates, pregnancy loss, and gender ratio after synchronization of ovulation in lactating dairy cows," *J. Dairy Sci.*, 81:2139-2144 (Abstract only).
Santos et al. (2001) "Effectd of human chorionic gonadotropin on luteal function and reproductive performance of high-producing lactating Holstein dairy cows"; *J. Animal Science* 79:2881-2894.
Staples et al. (1990) "Relationship between ovarian activity and energy status during the early postpartum period of high producing dairy cows," *J. Dairy Sci.*, 73:938-947.
Thatcher et al. (2001) "Effects of Hormonal Treatments on Reproductive Performance and Embryo Production"; *Theriogenology* 55:75-89.
Vasconcelos et al. (1997) "Pregnancy rate, pregnancy loss, and response to heat stress after AI at 2 different times from ovulation in dairy cows" *Biol. Reprod.*, 56 (Supp.1):140.
Weems et al. (1998) "Effect of Luteinizing Hordmone (LH), $PGE_2$, 8-EPI-$PGE_1$, 8-EPI-$PGE_2$ Trichosanthin, and Pregnancy Specific Protein B (PPB) on Secretion of Progesterone in vitro by Corpora Lutea (CL)( from Nonpregnant and Pregnant Cows"; *Prostaglandins and other Lipid Mediators* 55:27-42.
Wolfenson et al. (2000) "Impaired reproduction in heat-stressed cattle: basic and applied aspects," *Anim. Reprod. Sci.*, 60-61:535-547.
International Preliminary Report for corresponding PCT/US2008/053417 application, issued Aug. 11, 2009.
Ben-Menahem et al. (2006) *Biology of Reproduction*, 39th Annual Meeting of the Society for the Study of Reproduction; Omaha, NE, Jul. 29-Aug. 1, 2006, Abstract 77.
Esch et al. (1986) *Proc Natl Aced Sci USA*, 83:6618-6621.
Kanda et al. (1999) *Molecular Endocrinology*, 13(11):1873-1881.
Wilson et al. (1993) *Animal Reprod Sci*, 33:71-82.

* cited by examiner

*Primary Examiner* — Bridget E Bunner
*Assistant Examiner* — Christina Borgeest
(74) *Attorney, Agent, or Firm* — Lathrop & Gage LLP

(57) ABSTRACT

The present invention provides methods of producing biologically active recombinant bFSH and methods of increasing reproduction in mammals, particularly bovine, using recombinant bFSH. Also provided are methods of producing single chain recombinant bFSH. The recombinant bFSH of the present invention increases superovulation, embryo development, and reproductive efficiency in cattle and other ungulates.

20 Claims, 5 Drawing Sheets

```
atgaagtctgtccagttctgtttccttttctgttgctggagagcaatctgctgcagaagc
 M  K  S  V  Q  F  C  F  L  F  C  C  W  R  A  I  C  C  R  S
tgcgagctgaccaacatcaccatcacggtggagaaagaggaatgtggcttctgcataagc
 C  E  L  T  N  I  T  I  T  V  E  K  E  E  C  G  F  C  I  S
atcaacaccacgtggtgtgcaggctactgctacacccgggacttggtgtacagggaccca
 I  N  T  T  W  C  A  G  Y  C  Y  T  R  D  L  V  Y  R  D  P
gcaaggcccaatatccagaaaacgtgtaccttcaaggagctggtctacgagacggtgaaa
 A  R  P  N  I  Q  K  T  C  T  F  K  E  L  V  Y  E  T  V  K
gtgcctggctgtgctcaccatgcagactccctgtacacgtacccagtagccactgaatgt
 V  P  G  C  A  H  H  A  D  S  L  Y  T  Y  P  V  A  T  E  C
cactgcagcaagtgcgacagcgacagcactgactgcaccgtgcgaggcctggggcccagc
 H  C  S  K  C  D  S  D  S  T  D  C  T  V  R  G  L  G  P  S
tactgctccttcagggaaatcaaagaatcctcttcctcaaaggccccctcccccgagcctt
 Y  C  S  F  R  E  I  K  E  S  S  S  S  K  A  P  P  P  S  L
ccaagtccatcccgactcccggggccctcggacacccccgatcctcccacaatttcctgat
 P  S  P  S  R  L  P  G  P  S  D  T  P  I  L  P  Q  F  P  D
ggagagtttacaatgcagggctgtcctgaatgcaagctaaaagaaaacaaatacttctcc
 G  E  F  T  M  Q  G  C  P  E  C  K  L  K  E  N  K  Y  F  S
aagccagatgctccaatctatcagtgcatggggtgctgcttctccagggcatacccccact
 K  P  D  A  P  I  Y  Q  C  M  G  C  C  F  S  R  A  Y  P  T
ccagcgaggtctaagaagacaatgttggtccccaagaacatcacctcggaagctacatgc
 P  A  R  S  K  K  T  M  L  V  P  K  N  I  T  S  E  A  T  C
tgtgtggccaaagcatttaccaaggccacagtgatgggaaatgtcagagtggagaaccac
 C  V  A  K  A  F  T  K  A  T  V  M  G  N  V  R  V  E  N  H
Accgagtgccactgcagcacttgttattatcacaaatcctga (SEQ ID NO:11)
 T  E  C  H  C  S  T  C  Y  Y  H  K  S  - (SEQ ID NO:10)
```

FIG. 1

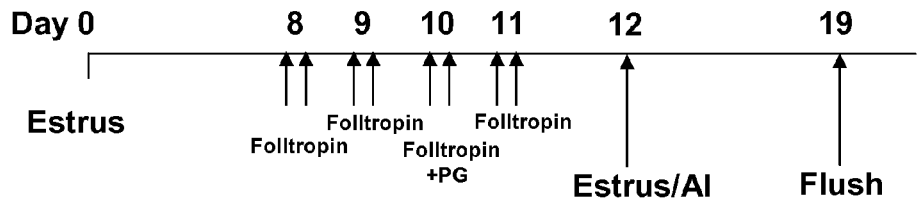
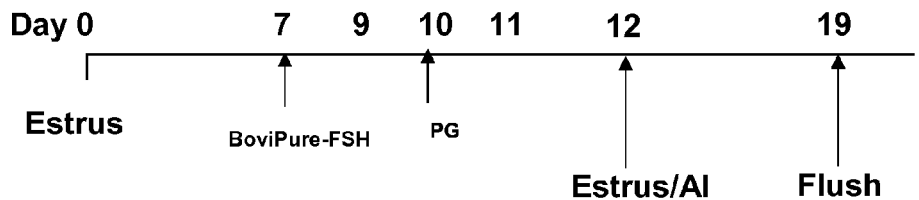
FIG. 5
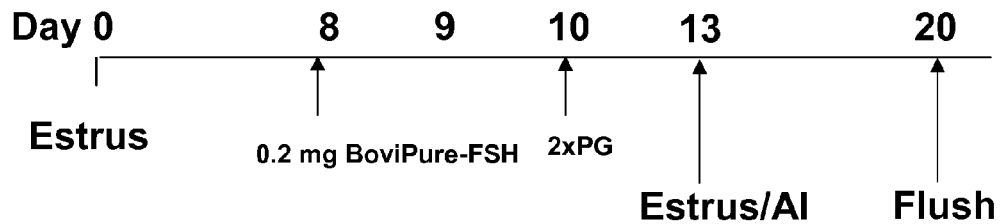
FIG. 6

METHODS FOR INDUCING SUPEROVULATION IN UNGULATES

CROSS-REFERENCE TO RELATED APPLICATIONS

This application claims the benefit of U.S. Provisional Application 60/888,807, filed Feb. 8, 2007, which is hereby incorporated by reference to the extent not inconsistent with the disclosure herein.

STATEMENT REGARDING FEDERALLY SPONSORED RESEARCH OR DEVELOPMENT

Not Applicable

BACKGROUND OF THE INVENTION

The field of embryo transfer is growing in each animal sector in which multiple offspring are desirable. There were over 130,000 donor cattle superovulated worldwide in 2006 and the number of transferred embryos increased by 10% to over 670,000 (IETS Newsletter December 2007). In the United States, there were an estimated 52,000 donors superovulated in 2006 (AETA Annual Report 2006). The current superovulation protocols all require multiple injections of Follicle Stimulating Hormone (FSH) twice daily over the course of at least 4 days. The FSH currently used is animal derived, impure and has the propensity to be infectious. The invention described herein is a long-acting FSH analog that is effective in causing superovulation with a single injection. Furthermore, this FSH analog is highly purified and free of infectious vectors and other contaminants.

There are over nine million dairy cows in the United States, over one million in Canada and over fifty million worldwide. The dairy industry is extremely competitive and the ability of a dairy to increase the efficiency of breeding and to maintain pregnancies post insemination is critical to the profitability of the producer. It is estimated that the cost of a non-pregnant cow is about five dollars per day. It is further estimated that current inseminations result in approximately twenty to thirty-five percent pregnant cows at day 45 and of those cows ninety to ninety-five percent deliver calves at the end of the 283-day gestation period. However, reproductive efficiency in dairy cattle has been declining steadily over a prolonged period of time. The magnitude and the consistency of this trend are of great importance to the dairy industry and amount to a steady decline of approximately one percent in first service conception rates per year for the last ten years. The impact of this change in productivity has not been readily apparent, because individual cow milk production has increased by twenty percent over the same period. In the long run, the dairy industry cannot afford to continue the current rate of declining reproductive performance.

Declining reproductive efficiency of dairy cattle has been observed throughout the United States, and other parts of the world where milk production has been increasing (Lucy, M. C. (2001) "Reproductive loss in high-producing dairy cattle: Where will it end?," *J. Dairy Sci.*, 84:1277-1293; Roche et al. (2000) "Reproductive management of postpartum cows," *Anim. Reprod. Sci.*, 60-61:703-712; Royal et al. (2000) "Declining fertility in dairy cattle: changes in traditional and endocrine parameters of fertility," *Anim. Sci.*, 70:487-502; and Macmillan et al. (1996) "The effects of lactation on the fertility of dairy cows" *Aust. Vet. J,* 73:141-147). Numerous features may negatively influence fertility in dairy cows, including negative energy balance and disease events such as retained placenta, ketosis, cystic ovary, and mastitis (Lucy 2001, supra; and Staples et al. (1990) "Relationship between ovarian activity and energy status during the early postpartum period of high producing dairy cows," *J. Dairy Sci.*, 73:938-947). Furthermore, a prominent trend in the U.S. dairy industry is decreased number of dairy farms, steadily increasing herd size, and movement of dairy production to the western states (USDA National Agricultural Statistics Service, http//www.usda.gov/nass). Larger herd size may contribute to decreased reproductive performance because of the associated changes in the dairy labor force and cow management, resulting in poorly trained or over tasked workers identifying estrus behavior, performing artificial insemination, conducting estrus synchronization programs, and identifying and treating sick cows (Lucy 2001, supra). Heat stress, which occurs throughout much of the year in western and southwestern US dairy herds, has significant negative impact on cattle fertility (Wolfenson et al. (2000) "Impaired reproduction in heat-stressed cattle: basic and applied aspects," *Anim. Reprod. Sci.,* 60-61:535-547).

The primary revenue source in the dairy industry is milk production. Progress in genetics and management of dairy cows has led to remarkable increases in milk production throughout the last several decades, with a twenty percent increase in per-cow production in the last ten years alone (USDA National Agricultural Statistics Service, http//www.usda.gov/nass). In order to maintain high herd productivity, however, cows must become pregnant and deliver a calf so that the lactation cycle is renewed. Additionally, sufficient numbers of heifers must be produced to replace older cows. Therefore, the future productivity of the dairy industry is very dependent on the maintenance of fertility and reproduction.

The ability to increase reproductive performance in horses, cattle or other ungulates would have a significant economic benefit to owners. This can be achieved through increasing fertility as well as improving pregnancy maintenance throughout the gestation period to prevent pregnancy losses. Recent studies with ultrasonic pregnancy detection demonstrate embryonic losses in cattle of at least 20% between 28 and 60 days of pregnancy (Pursley et al. (1998) "Effect of time of artificial insemination on pregnancy rates, calving rates, pregnancy loss, and gender ratio after synchronization of ovulation in lactating dairy cows," *J. Dairy Sci.,* 81:2139-2144; and Vasconcelos et al. (1997) "Pregnancy rate, pregnancy loss, and response to heat stress after AI at 2 different times from ovulation in dairy cows" *Biol. Reprod.,* 56 (Supp. 1):140). There are likely even higher losses prior to 28 days that are undetected by ultrasound examination (Lucy 2001, supra). Data suggest that modern dairy cows fail to establish pregnancy because of suboptimal uterine environment (Gustafsson, H. and K. Larsson (1985) "Embryonic mortality in heifers after artificial insemination and embryo transfer: differences between virgin and repeat breeder heifers," *Res. Vet. Sci.,* 39:271-274). Although there are numerous possible factors that could be responsible for embryonic losses, one potential cause is low blood progesterone concentration.

Currently, several hormone therapies are used to increase fertility or to maintain pregnancy. Thatcher et al. (2001 Theriogenology 55:75-89) describes the effects of hormonal treatments on the reproductive performance of cattle. Hormonal treatments include administration of bovine somatotrophin (bST) and human chorionic gonadotropin (hCG). D'Occhio et al. (2000 Anim. Reprod. Sci. 60-61:433-442) describes various strategies for beef cattle management using gonadotropin releasing hormone (GnRH) agonist implants. De Rensis et al. (2002 Theriogenology 58(9):1675-1687) describes the effect on dairy cows of administering GnRH or hCG before artificial insemination. Martinez et al. (1999 *Anim. Reprod. Sci.* 57:23-33) describes the ability of porcine luteinizing hormone (LH) and GnRH to induce follicular wave emergence in beef heifers on Days 3, 6, and 9 of the estrus cycle, after ovulation (Day 0), without insemination. Santos et al. (2001 J. Animal Science 79:2881-2894) describes the effect on reproductive performance of intramuscular administration of 3,300 IU of hCG to high-producing dairy cows on Day 5 after artificial insemination. Lee et al. (1983 Am. J. Vet. Res. 44(11):2160-2163) describes the effect on dairy cows of administering GnRH at the time of artificial insemination. U.S. Pat. No. 5,792,785 (issued Aug. 11, 1998) and U.S. Pat. No. 6,403,631 (issued Jun. 11, 2002) describe methods and compositions for administering melatonin before and after insemination to enhance pregnancy success in an animal. Chagas e Silva et al. (2002 *Theriogenology* 58(1):51-59) describes plasma progesterone profiles following embryo transfer in dairy cattle. Weems et al. (1998 Prostaglandins and other Lipid Mediators) describes the effects of hormones on the secretion of progesterone by corpora lutea (CL) from non-pregnant and pregnant cows. U.S. Pat. No. 4,780,451 (issued Oct. 25, 1988) describes compositions and methods using LH and follicle stimulating hormone (FSH) to produce superovulation in cattle. Farin et al. (1988 *Biol. Reprod.* 38:413-421) describes the effect on ovine luteal weight of intravenous administration of 300 IU of hCG on Days 5 and 7.5 of the estrus cycle, without insemination. Hoyer and Niswender (1985 *Can. J. Physiol. Pharmacol.* 63(3):240-248) describe the regulation of steroidogenesis in ovine luteal cells. Juengel and Niswender (1999 *J. Reprod. Fertil. Suppl.* 54:193-205) describe the molecular regulation of luteal progesterone in domestic ruminants. U.S. Pat. No. 5,589,457 (issued Dec. 31, 1996) describes methods for synchronizing ovulation in cattle using GnRH, LH, and/or hCG and PGF2α.

Many of these treatments use hormones or hormone analogs from the glycoprotein hormone family, which consists of the pituitary proteins luteinizing hormone (LH), follicle-stimulating hormone (FSH), thyroid stimulating hormone (TSH) and chorionic gonadotropin (CG). The gonadotropins, which include CG, FSH and LH, are essential for reproductive function. They are heterodimers composed of two non-covalently associated α and β subunits. Both subunits are glycosylated, containing asparagine (N)-linked oligosaccharides and, in the case of the CGβ subunit, O-linked carbohydrates are also present in a cluster of amino acids at the C-terminus. The individual human β subunits are encoded by separate genes, and the LHβ and CGβ proteins are structurally and functionally similar; having more than 80% amino acid identity (Pierce J G, Parsons (1981) "Glycoprotein hormones: structure and function," Biochem. 50:465-495). Within a species, the α subunit amino acid sequence is common to all four hormones (Pierce J G, Parsons (1981) Biochem. 50:465-495).

In order to use gonadotropins to improve reproduction efficiency in animals, the availability of purified proteins is essential. Currently, the sources for gonadotropins are serum and whole pituitary extracts. To obtain sufficient quantities of these native hormones for such work is expensive and difficult. Pituitary extracts can be effective reproductive therapeutics but contain contaminants and may vary in their amounts of LH and FSH. Preparations of pure pituitary gonadotropins without cross-contamination are not readily available. Given the problem of animal-to-animal variation of native gonadotropins and the charge heterogeneity in the N-linked carbohydrates, the ability to generate the corresponding recombinant proteins will yield gonadotropins of a more homogeneous composition that can be standardized with respect to mass and bioactivity. Such proteins will be critical for calibrating clinical laboratory assays and for breeding management, such as shortening the time to ovulation in transitional and cycling mares for natural breeding and artificial insemination. The use of recombinant forms, as opposed to hormones extracted from serum and pituitary tissue, would avoid the co-contamination of pathogens and agents with a propensity to cause prion related diseases.

Thus, what are needed are active recombinant gonadotropin analogs, particularly FSH analogs, and methods of using such analogs to improve reproduction of cattle and other animals.

SUMMARY OF THE INVENTION

The present invention provides embodiments of compositions and methods including bovine FSH (bFSH) analogs, particularly single chain recombinant bFSH analogs. Such active recombinant bFSH analog products are beneficial for improving reproduction activity, superovulation and embryo production in bovine and other mammalian species. Recombinant bFSH analogs also avoid cross contamination issues and do not elicit a strong immune response in treated animals.

In embodiments, the present invention provides methods of using bovine FSH analogs to increase reproductive activity in ungulates, specifically cattle. In particular, a single chain bFSH analog is used to stimulate superovulation, increase embryo production, and increase reproduction in female animals. Administering bFSH in order to increase reproduction, the number of embryos or inducing superovulation is desirable in a number of species including, but not limited to bovine, sheep, goats, cervids, yaks, water buffaloes, bison, antelopes, gazelles, elk, reindeer, moose, bighorn sheep, giraffes, and camelids including bactrian and dromedary camels, llamas, swine, equine, alpacas, and vicunas. This method is particularly effective for increasing superovulation, embryo production, and pregnancies in bovine. The bFSH analogs used in embodiments of the present invention are at least 95% pure and are preferably recombinant polypeptides. More preferably, the bFSH analog is a single chain recombinant bFSH. In embodiments, the present invention also provides methods of producing biologically active single chain recombinant bFSH.

One embodiment of the invention provides a method of making recombinant bFSH analogs by expressing DNA encoding the bFSH alpha and beta subunits. In one embodiment, a single chain recombinant bFSH analog is produced where the alpha subunit is linked to the beta subunit using a linker peptide. Native FSH is produced as separate alpha and beta subunits which non-covalently assemble together. The single chain recombinant bFSH of the present invention has a high level of expression and bioactivity. In one embodiment, a recombinant bFSH analog (named bFSHβCTPα) is a single chain recombinant bFSH where the alpha and beta subunits from bovine FSH are linked together using a human chorionic gonadotropin carboxy terminal peptide.

The amino acid sequences for the bFSH alpha and beta subunits are given as SEQ ID NO: 1 and SEQ ID NO: 2, respectively. It is understood that a bFSH analog may have minor differences in the amino acid sequence without affecting function. In one embodiment, the single chain bFSH analog has alpha and beta subunits that are at least 80% identical in sequence to the bovine FSH alpha and beta subunits (SEQ ID NO: 1 and SEQ ID NO: 2). Preferably the bFSH analog comprises a first polypeptide having at least 85% homology with SEQ ID NO: 1 and a second polypeptide having at least 85% homology with SEQ ID NO: 2. More preferably, the first polypeptide has at least 90% homology with SEQ ID NO: 1 and the second polypeptide has at least 90% homology with SEQ ID NO: 2. Even more preferably, the first polypeptide has at least 95% homology with SEQ ID NO: 1 and the second polypeptide has at least 95% homology with SEQ ID NO: 2.

Preferably, the bFSH analog is a single chain where the first polypeptide and second polypeptide are covalently linked. By covalently linked, it is meant that the first polypeptide is attached to the second polypeptide directly or through a linker peptide, where one end of the linker peptide is attached to the first polypeptide and the other end of the linker peptide is attached to the second polypeptide. Linker peptides able to attach to polypeptides in recombinant protein synthesis are well known in the art, and any linker peptide suitable to be expressed as part of the bFSH analog may be used. In one embodiment, the peptide linker is human chorionic gonadotropin carboxy terminal peptide (CTP). It should be understood that the positions of the alpha and beta subunit are reversible, in that the bFSH analog may have the configuration (alpha subunit)-linker-(beta subunit) or (beta subunit)-linker-(alpha subunit).

The amino acid sequences of the bFSH subunits are provided herein. Accordingly, one skilled in the art will be able to discern the DNA and RNA sequences that encode the bFSH analogs. In one embodiment, the nucleic acid molecules coding for the bFSH analog are incorporated into an expression vector which is transfected into a cell or cell line able to express the vector.

In one embodiment, a bFSH analog is used to produce a superovulation event that results in the recovery of viable embryos. In another embodiment, a bFSH analog is used to increase embryo production. Inducing superovulation and increasing embryo production are useful for embryo transplantation and in vitro fertilization. In one embodiment, an effective amount of a bFSH analog is administered to one or more ungulates, preferably bovine, in order to increase reproduction. In previously known methods, FSH must be administered in multiple doses spread out over several days. In the present invention, only a single dose of the single chain recombinant bFSH analog is needed to be administered to the animals for each estrus cycle. This can be attributed to increased activity or longer lasting activity by the FSH analog. In one embodiment, animals are prepared for the FSH analog injection by identifying the reference heat date (day of last heat) and then the bFSH analog is administered in a single injection on a day between about day 7 and about day 13 of the animal's cycle. Two luteolytic doses (approximately 12 hours apart) of prostaglandin are optionally given to the animal approximately 2 to 5 days after the FSH administration. The animals are checked for signs of heat and then bred by natural or artificial insemination. In a further embodiment, insemination occurs approximately 4 to 6 days after administration of the bFSH. In another further embodiment, the embryos are flushed approximately 6-8 days after heat.

Additional hormones, such as luteinizing hormone, chorionic gonadotropin and prostaglandin, are optionally administered as well as the bFSH analog. In one embodiment, prostaglandin is administered to the animal in addition to administration of the bFSH analog. The prostaglandin is optionally administered as a single dose, typically by injection, or as multiple doses administered several hours apart. In one embodiment, a first dose of prostaglandin is given to the animal after administration of the bFSH analog followed by a second dose of prostaglandin which is given to the animal approximately 6 hours to 1 day following the first prostaglandin dose.

In one embodiment, between about 0.01 μg and about 5 mg of the bFSH analog is administered to the one or more animals. Preferably between about 1.0 μg and about 0.2 mg of the bFSH analog is administered, more preferably between about 10 μg and about 150 μg. The bFSH analog can be administered using any means known in the art, including but not limited to intramuscular injection and intravenous injection. Preferably the bFSH analog is administered through intramuscular injection.

Another embodiment provides a kit for inducing superovulation or increasing the number /of embryos in a single estrus cycle in a mammal such as a bovine comprising: at least one dose comprising an effective amount of single chain recombinant bFSH analog comprising a first polypeptide having at least 90% homology with SEQ ID NO: 1, and a second polypeptide having at least 90% homology with SEQ ID NO: 2, wherein the first and second polypeptides are covalently linked; a device for administering a single dose of the bFSH analog; and instructions for administering the dose of the bFSH analog. In an embodiment, the effective amount of the bFSH analog in each dose is between about 1 μg and about 0.2 mg, preferably between about 10 μg and about 150 μg, and can vary depending on the kit. The device for administering the dose to the animal can be any device known in the art, such as needles and syringes. Optionally, the device is an injection device suitable for delivering a single dose of the bFSH analog. The kit may also comprise components such as additional hormones, such as prostaglandin, and injection devices for administering additional hormones.

In an embodiment, a composition of the invention is isolated or purified. In an embodiment, a composition of the invention comprises a protein composition as described herein, such as a bFSH composition, in a pharmaceutical formulation. In an embodiment, the invention provides a pharmaceutical formulation comprising a composition of the invention. In an embodiment, the invention provides a method of synthesizing a composition of the invention or a pharmaceutical formulation thereof. In an embodiment, a pharmaceutical formulation comprises one or more excipients, carriers, and/or other components as would be understood in the art. Preferably, the components meet the standards of the National Formulary ("NF"), United States Pharmacopoeia ("USP"), or Handbook of Pharmaceutical Manufacturing Formulations. In an embodiment, an effective amount of a composition of the invention can be a therapeutically effective amount. In an embodiment, the invention provides a method for treating a medical condition comprising administering to a subject in need thereof, a therapeutically effective amount of a composition of the invention. In an embodiment, the invention provides a medicament which comprises a therapeutically effective amount of one or more compositions of the invention. In an embodiment, the invention provides a method for making a medicament for a purpose or treatment of a condition described herein.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE DRAWINGS

FIG. 1 shows sequence information for coding sequence of recombinant bFSHβCTPα. The lower case letters represent the nucleic acid (cDNA) sequence and the upper case letters show the amino acid sequence. The carboxy terminal hCG peptide, which links the beta and alpha subunits, is underlined. The underlined amino acids indicate the peptide that links the beta (β) and alpha (α) subunits. The underlined nucleotides encode the signal peptide.

FIG. 5 illustrates one administration protocol where recombinant bFSHβCTPα (referred to as BoviPure-FSH) and Folltropin®-V are administered to bovine. Folltropin is first administered starting on day 8 after estrus, and bFSHβCTPα administered 7 days after estrus. Artificial insemination (estrus/AI) occurs at day 12 and embryos are flushed at day 19. As shown, bFSHβCTPα only requires a single administration, while Folltropin requires a series of 8 doses between day 7 and day 11.

FIG. 6 illustrates one experiment where 0.2 mg of recombinant bFSHβCTPα (referred to as BoviPure-FSH) is administered to 21 cows between 7-8 days after estrus. Artificial insemination occurs on day 13 and embryos are flushed on day 20. The resulting number of viable embryos is slightly greater than the number of unfertilized ova, indicating that a single treatment of bFSHβCTPα is sufficient for follicular development and that animals exhibited the expected estrus timing after administration of prostaglandin.

DETAILED DESCRIPTION

Figure 2:
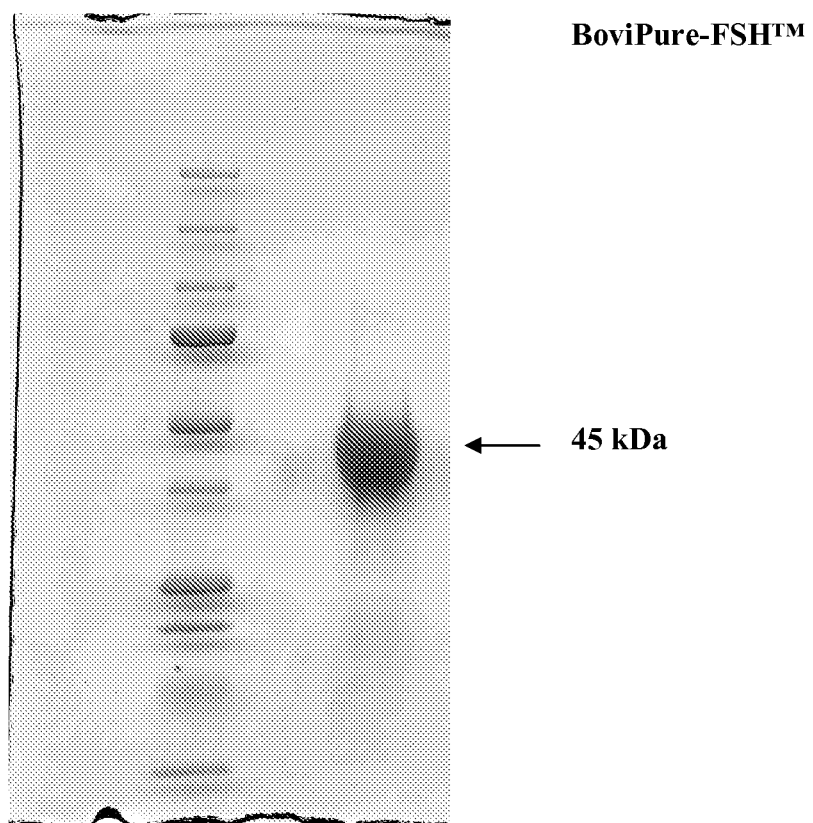
FIG. 2 is SDS-PAGE analysis of recombinant bFSHβCTPα showing a single predominant product at approximately 45 kDa.

As used herein, "breeding" refers to methods known in the art that pertain to making a female animal pregnant. Such methods include natural and artificial insemination. Breeding methods may include a waiting time after observation of behavioral estrus or after forcing estrus.

As used herein, "estrus" refers to the period during which an animal is most likely to become pregnant. As used herein, "forcing estrus" refers to methods known in the art for forcing heat. Forcing estrus can include waiting periods, as appropriate. As used herein, "behavioral estrus" refers to the behavioral demonstration that an animal is in heat, including showing standing heat. As used herein, "Day 0" is the day that an animal is in behavioral estrus.

As used herein, "cow" refers to female bovines, including heifers.

As used herein, "pregnant mammal" refers to a mammal that is currently pregnant and also includes a mammal that has been inseminated and may be pregnant or to a plurality of inseminated mammals, some of which are likely to be pregnant.

As used herein, "increasing reproduction" refers to increasing the likelihood that an animal, or a plurality of animals, which has been inseminated will become pregnant, will deliver a live offspring, or develop viable embryos. Increasing reproduction also refers to increasing the number of viable embryos an animal or plurality of animals produce.

As used herein, "superovulation" refers to increasing the number of ovulated follicles and the creation multiple fertile ova. By "superovulation" it can also mean producing multiple embryos from a single injection of bFSH.

As used herein, "effective amount" refers to an amount of bFSH that is effective to produce the desired outcome.

As used herein, "administering" refers to any method of administering a therapeutic to an animal known in the art. Examples of administering include, but are not limited to, injecting the therapeutic subcutaneously, intramuscularly and intravenously.

As used herein, "analog" refers to a compound which mimics the physiological effect of a natural compound. Analogs will typically be structurally similar to the natural compound but may have structural or chemical differences as a result of production methods or because the differences confer a beneficial activity to the analog.

As used herein, "about 95% pure" refers to purity as measured by any method known in the art, including but not limited to protein electrophoresis.

As used herein, "insemination" refers to introducing semen by any method known in the art, including, but not limited to, natural and artificial insemination.

The single chain recombinant bFSH analogs of the present invention induce superovulation, increase embryo production, and increase reproduction in female bovine using a single administration of a single dose. Current FSH regimes typically require multiple doses over several days at approximately 12 hour intervals. Field studies indicate that using recombinant bFSH analogs of the present invention are able to achieve superovulation using smaller amounts of bFSH with an easier and more efficient administration.

The cDNA nucleotide sequence and amino acid sequence for bFSHβCTPα (also referred to as BoviPure-FSH™) is provided in FIG. 1 and the amino acid sequence is further provided in SEQ ID NO: 10. As shown in FIG. 1, the first section (amino acids 1-129) corresponds to the bovine FSH beta subunit (SEQ ID NO: 2), the underlined section corresponds to the carboxy terminal peptide linker (amino acids 130-157, SEQ ID NO: 3), and the third section (amino acids 158-253) corresponds to the bovine FSH alpha subunit (SEQ ID NO: 1).

One embodiment of the invention encompasses a single chain recombinant bFSH analog having the amino acid sequence of SEQ ID NO: 10, or an amino acid sequence having 90% or greater, preferably 95% or greater, homology to the amino acid sequence of SEQ ID NO: 10. Another embodiment is a nucleic acid or a vector comprising a nucleic acid encoding a single chain amino acid having 90% or greater, preferably 95% or greater, homology to the amino acid sequence of SEQ ID NO: 10. Another embodiment is a nucleic acid or a vector comprising a nucleic acid encoding a single chain amino acid having a first polypeptide with 90% or greater homology, preferably 95% or greater homology, to SEQ ID NO: 1 and a second polypeptide with 90% or greater homology, preferably 95% or greater homology, to SEQ ID NO: 2. Also encompassed are functional single chain recombinant bFSH analogs encoded by fragments of the nucleotide sequence provided in SEQ ID NO: 10.

EXAMPLE 1

Engineering Single-Chain Recombinant bFSHβCTPα

The cDNA encoding bovine FSHβ subunit was amplified from bovine pituitary cDNA, which was generated using an iScript cDNA Synthesis Kit (Bio-Rad Laboratories, Hercules, Calif.). Amp was performed using Deep Vent DNA polymerase (New England Biolabs, Ipswich Mass.) and Techgene model FTGENE2D thermal cycler (Techne, Burlington, N.J., USA). 2 uM of each of the following primers was used in the FSHβ amplification: 5'-GTG CAT AGG ATG AAG TCT GTC C-3' (SEQ ID NO: 4) and 5'-GGC GCG TTA TTC TTT GAT TTC CC-3' (SEQ ID NO: 5). PCR conditions were as follows: initial denaturation 94° C. 5 min., cycle 1-30 denaturation 94° C. 30 sec., annealing 55° C. 30 sec., extension 72° C. 30 sec, and the final extension 72° C. 5 min. The FSHβ □PCR product was cloned into PCR-Script vector (Stratagene, La Jolla, Calif.) and sequenced for verification. To construct the recombinant bFSHβCTPα single chain, a bLH template was used as one of two PCR templates for overlapping PCR. The other template was pCRScript-bFSHβ as mentioned above. The following primers were used in the construction of the recombinant bFSHβCTPα single chain:

```
Primer 1
                                       (SEQ ID NO: 6)
5'-GC CGA AAG CTT ATT ATG AAG TCT GTC C-3'
            bFSHβ primer Primer 2
                                       (SEQ ID NO: 7)
5'-GAG GAA GAG GAT TCT TTG ATT TCC C-3'
     bFSHβ (bold)/bLHCTPα overlapping primer Primer 3
                                       (SEQ ID NO: 8)
5'-GGG AAA TCA AAG AAT CCT CTT CCT C-3'
 bFSHβ (bold)/bLHCTPα overlapping primer Primer 4
                                       (SEQ ID NO: 9)
5'-CGT GCT GGA TCC TTA TTA GGA TTT GTG-3'
            bLHCTPα primer
```

In the first PCR reaction, PCR-Script-bFSH was used as the template with primers 1 and 2 to amplify PCR product A containing a 5' HindIII restriction site, the bFSHβ coding sequence with the stop codon removed (TAA), and overlapping bLHCTPα sequence. In a parallel reaction, the bLH cDNA was used as the template with primers 3 and 4 to amplify PCR product B containing a BamHI restriction site added to the 3' end, overlapping bFSHα sequence (in bold, above), and bLHCTPα coding sequence with an additional stop codon (TAA) added. The overlapping PCR was performed using fragments A and B with primers 1 and 4 resulting in the final recombinant product bFSHβCTPα. The PCR (A and B) conditions were the same as above for bFSHβ. The PCR product was digested with HindIII and BamHI, inserted into shuttle vector and sequenced for verification. The final sequence is shown in FIG. 1. In one embodiment, the present invention comprises a protein encoded by the nucleotide sequence of FIG. 1 or peptides or fragments thereof having at least 90% similarity to the amino acid sequence of FIG. 1 (SEQ ID NO: 10).

Expression and Purification of Recombinant bFSHβCTPα

The recombinant bFSHβCTPα served as template DNA for further amplification and subcloning into the proprietary GPex® expression system at Gala Design/Cardinal Health-Middleton. This system is described in U.S. Pat. No. 6,852,510B2.

Cell culture supernatant was purified using SP-Sepharose Fast Flow resin (Amersham Biosciences, Sweden) in a suitable chromatography column. The total protein load was maintained below 30 mg/ml of resin. The column was equilibrated with a 0.1M NaCl, 8 mM $C_2H_3NaO_2$ buffer at pH 4.5 at a flow rate of 90 cm/hr. Cell culture supernatant was adjusted to pH 4.5 with concentrated acetic acid and loaded onto the column at a flow rate of 60 cm/hr. The column was washed with 0.1M NaCl, 8 mM $C_2H_3NaO_2$, pH 4.5 for three column volumes. Two additional wash buffers were then applied to the column: a 0.1M $NaH_2PO4$ buffer at pH 5.5 for three column volumes followed by a 0.16M NaCl, 8 mM $C_2H_3NaO_2$ buffer at pH 4.5 for three column volumes. After the final wash, a five-column volume linear gradient between the 0.16M NaCl, 8 mM $C_2H_3NaO_2$ buffer and a 0.8M NaCl, 8 mM $C_2H_3NaO_2$, pH 4.5 buffer was performed to elute the recombinant bFSHβCTPα from the resin. The recombinant bFSHβCTPα that elutes during this step is 95% pure by SDS-PAGE analysis. Identity of the recombinant bFSHβCTPα was confirmed by ELISA, immunoblotting and MALDI-TOF analysis. As shown in FIG. 2, expression of this nucleotide sequence predominantly produces a single product at approximately 45 kDa.

Bioactivity of bFSHβCTPα

Figure 3:
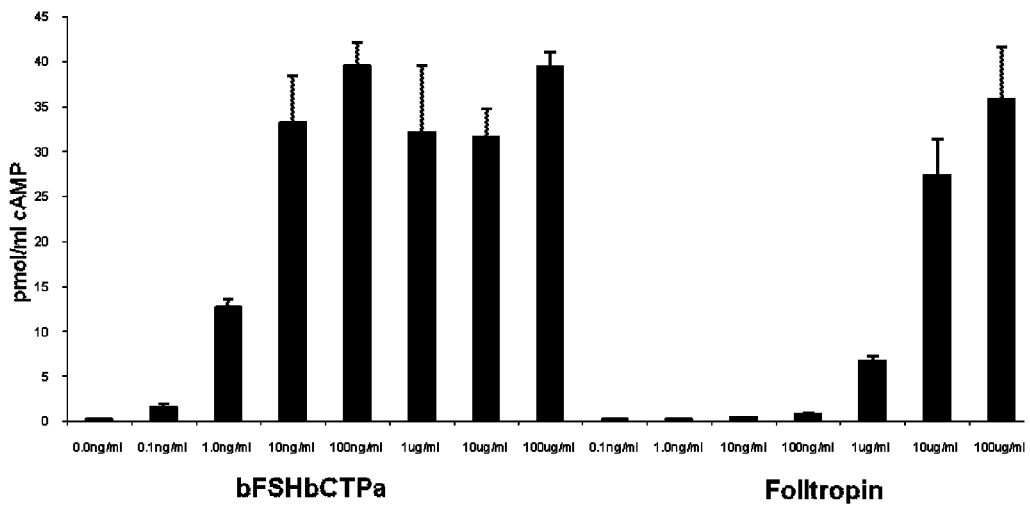
FIG. 3 is a bioactivity comparison in an in vitro assay between bFSHβCTPα and Folltropin®-V, a commercial porcine FSH preparation (Bioniche Animal Health). The assay utilizes FSH receptors that produce cAMP when a FSH analog is bound by the receptor. Recombinant bFSHβCTPα showed greater activity measured by the amount of released cAMP, especially at analog amounts of 1 µg/ml and below.

The bioactivity of bFSHβCTPα was compared to Folltropin®-V, a commercial porcine FSH preparation (Bioniche Animal Health), in an in vitro assay. The assay utilizes FSH receptors that produce cAMP when a FSH analog is bound by the receptor. Recombinant bFSHβCTPα showed greater activity measured by the amount of released cAMP, especially at analog amounts of 1 μg/ml and below. As shown in FIG. 3, Folltropin had low activity at 1 μg/ml and significant activity at 10 μg/ml and 100 μg/ml. Folltropin had no significant activity below 1 μg/ml. In comparison, bFSHβCTPα appeared to have the same or slightly increased activity at 100 μg/ml, significantly greater activity at 1 μg/ml and 10 μg/ml, and showed activity at amounts as low as 1.0 ng/ml.

Figure 4:
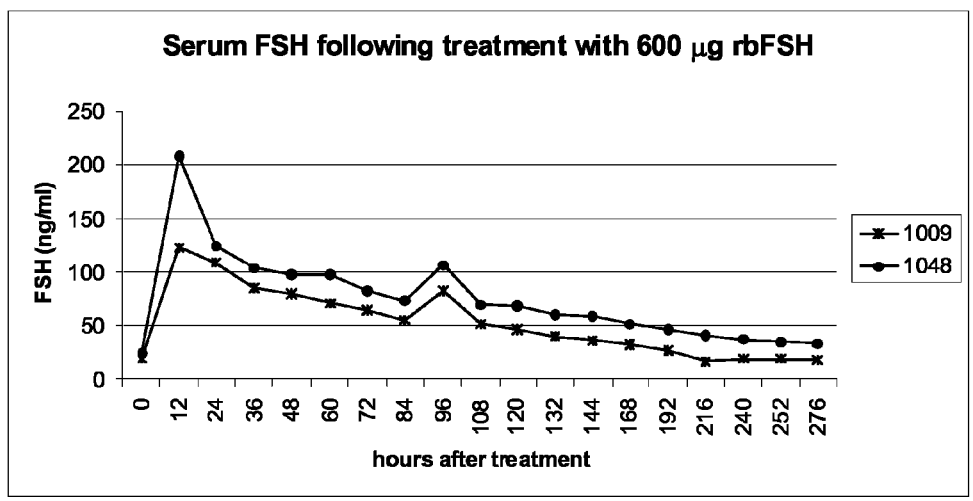
FIG. 4 shows serum FSH concentration levels following administration of 600 µg of a recombinant bFSH analog of the present invention in two different bovine. Ovulation was induced by administration of prostaglandin approximately 4 days (96 hours) after administration of the bFSH analog.

FIG. 4 shows serum FSH concentration levels following administration of 600 μg of recombinant bFSH analog of the present invention in two different bovine. The serum levels of FSH spiked immediately at approximately 12 hours following administration. Ovulation was induced by administration of prostaglandin approximately 4 days after administration of bFSH.

EXAMPLE 2

Comparative Effects of bFSHβCTPα and Folltropin in Bovine

The effects of Folltropin and bFSHβCTPα on bovine were compared. In one experiment, both products are administered to the animals starting approximately 7-8 days after estrus as illustrated in FIG. 5. Prostaglandin is administered at approximately day 10 (approximately 2-3 days after the first dose of the bFSH analog) and artificial insemination occurs at about day 12 (approximately 4-6 days after administration of the bFSH analog). The embryos and ova are flushed at about day 19 (approximately 11-13 days after administration of the bFSH analog), and the respected number of viable embryos counted. Administration of both Folltropin and bFSHβCTPα result in successful embryo production and superovulation in a population of animals, however, as shown in FIG. 5, only a single dose of bFSHβCTPα is administered, while Folltropin requires a series of 8 doses over a four day period.

FIG. 6 illustrates one experiment where 0.2 mg of bFSHβCTPα is administered to 21 angus beef cows. Administration of bFSHβCTPα occurs 7-8 days after estrus. Follicular development is checked approximately 2.5 days after administration of bFSHβCTPα, and luteolytic doses of prostaglandin administered 4 and 4.5 days after administration of bFSHβCTPα. The animals are checked for heat 5-6.5 days after administration of bFSHβCTPα and the animals inseminated after showing heat. Embryos are flushed 11-12 days after administration of the bFSH analog and counted.

Table 1 shows the number of recovered unfertilized ova compared with viable embryos from animals treated with bFSHβCTPα as described above and illustrated in FIG. 6. As shown in Table 1, the number of viable embryos was slightly greater than the number of unfertilized ova. This study establishes that a single treatment of bFSHβCTPα is sufficient for follicular development and that animals exhibited the expected estrus timing after administration of prostaglandin. More viable embryos/flush were observed with bFSHβCTPα than with a similar treatment with Folltropin. It was also observed that the animals receiving 0.2 mg of bFSHβCTPα developed overstimulation, indication that a lower dose of bFSHβCTPα may be preferable.

TABLE 1

| Cow ID | Total Ova Recovered | Unfertilized Ova | Viable Embyros * |
|---|---|---|---|
| BHR D156E | 27 | 14 | 12 |
| BHR 24J | 53 | 16 | 13 |
| BHR 51F | 1 | 1 | 0 |
| BHR H299 | 28 | 1 | 25 |
| BHR H311 | 30 | 0 | 24 |
| BHR M384 | 7 | 0 | 6 |
| BHR E454E | 36 | 21 | 5 |
| ASP 718 | 26 | 15 | 6 |
| ASP 400 | 8 | 8 | 0 |
| ASP 446 | 8 | 3 | 4 |
| ASP 142 | 19 | 19 | 0 |
| ASP 248 | 51 | 25 | 18 |
| ASP 990 | 23 | 4 | 9 |
| ASP 509 | 50 | 4 | 43 |
| ASP 653 | 19 | 9 | 1 |
| ASP 279 | 33 | 12 | 6 |
| ASP 186 | 21 | 3 | 14 |
| ASP 162 | 30 | 12 | 4 |
| ASP 380 | 31 | 6 | 12 |
| ASP 890 | 22 | 20 | 1 |
| ASP 164 | 35 | 20 | 13 |
| Subtotals | 558 | 213 | 216 |
| Averages | 26.57 | 10.14 | 10.29 |

EXAMPLE 3

Comparative Effects of bFSHβCTPα Doses in Bovine

Figure 7:
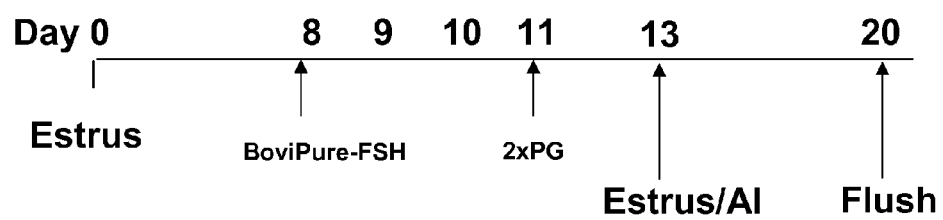
FIG. 7 illustrates one experiment where 5 cows are treated with 0.20 mg of bFSHβCTPα (also referred to as BoviPure-FSH), 5 cows are treated with 0.15 mg of bFSHβCTPα, and 5 cows are treated with 0.10 mg of bFSHβCTPα. The animals are administered bFSHβCTPα 7-8 days after estrus, and artificial insemination occurs 13 days after estrus. Two doses of prostaglandin are administered on day 11.

FIG. 7 and Table 2 illustrate a study where 5 cows were treated with 0.20 mg of bFSHβCTPα (labeled as FSH 200, numbers 1-5), 5 cows were treated with 0.15 mg of bFSHβCTPα (labeled as FSH 150, numbers 1-5), and 5 cows were treated with 0.10 mg of bFSHβCTPα (labeled as FSH 100, numbers 1-5). As illustrated in FIG. 7, the animals are administered bFSHβCTPα 7-8 days after estrus, and artificial insemination occurs 13 days after estrus. Two doses of prostaglandin are administered on day 11. As a control, 5 angus beef cows were treated with Folltropin (labeled as Folltropin, numbers 1-5). The number of recovered ova and viable embryos for each of these groups are shown in Table 2.

TABLE 2

| Cow ID | Total Ova Recovered | Viable Embryos |
|---|---|---|
| Folltropin 1 | no heat | |
| Folltropin 2 | 6 | 5 |
| Folltropin 3 | 6 | 6 |
| Folltropin 4 | 28 | 18 |
| Folltropin 5 | 18 | 13 |
| Subtotals | 58 | 42 |
| Averages | 14.5 | 10.5 |
| FSH 200 1 | 12 | 2 |
| FSH 200 2 | 15 | 14 |
| FSH 200 3 | no heat | |
| FSH 200 4 | overstim | no flush |
| FSH 200 5 | 53 | 8 |
| Subtotals | 80 | 24 |
| Averages | 26.7 | 8.0 |
| FSH 150 1 | 25 | 11 |
| FSH 150 2 | 8 | 7 |
| FSH 150 3 | 34 | 2 |
| FSH 150 4 | 50 | 4 |
| FSH 150 5 | 16 | 2 |
| Subtotals | 133 | 26 |
| Averages | 26.6 | 5.2 |
| FSH 100 1 | 5 | 4 |
| FSH 100 2 | 11 | 10 |
| FSH 100 3 | 6 | 5 |
| FSH 100 4 | 29 | 24 |
| FSH 100 5 | 46 | 42 |
| Subtotals | 97 | 85 |
| Averages | 19.4 | 17.0 |

The results show that 0.10 mg of bFSHβCTPα produced more viable embryos that the other regimes, including Folltropin. Overstimulation also was not observed at this dose.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known in the art including the compounds disclosed in the references disclosed herein are not intended to be included in the claim.

Any sequence listing information is part of the specification herein.

The invention claimed is:

1. A method of increasing reproduction in one or more ungulates comprising administering between 1 μg and 0.2 mg of a recombinant bFSH analog to said one or more ungulates between 7 to 13 days after start of estrus, wherein said bFSH analog comprises an amino acid sequence having at least 95% homology with SEQ ID NO: 10, wherein said ungulates are selected from the group consisting of bovine, equine, sheep and swine, wherein luteinizing hormone is not administered to said ungulates, and wherein administration of said bFSH analog increases the number of offspring produced by said one or more ungulates.

2. The method of claim 1 wherein said ungulates are bovine.

3. The method of claim 1 further comprising inseminating said one or more ungulates between 4 to 6 days after administering said bFSH analog.

4. The method of claim 1 wherein the amount of said bFSH administered between 7 to 13 days after start of estrus is between 10 μg and 150 μg.

5. The method of claim 1 wherein said bFSH analog is a recombinant polypeptide.

6. The method of claim 1 wherein only a single dose of the bFSH analog is administered to each ungulate in a single estrus cycle.

7. The method of claim 1 further comprising administering at least one injection of prostaglandin to said one or more ungulates.

8. A method of inducing superovulation in one or more ungulates comprising administering between 1 μg and 0.2 mg of a recombinant bFSH analog to said one or more ungulates between 7 to 13 days after start of estrus, wherein said bFSH analog comprises an amino acid sequence having at least 95% homology with SEQ ID NO: 10, wherein said ungulates are selected from the group consisting of bovine, equine, sheep and swine, wherein luteinizing hormone is not administered to said ungulates, and wherein administration of said bFSH analog increases the number of fertile ova produced by said one or more ungulates.

9. The method of claim 8 wherein said ungulates are bovine.

10. The method of claim 8 further comprising inseminating said one or more ungulates between 4 to 6 days after administering said bFSH analog.

11. The method of claim 8 wherein the amount of said bFSH administered between 7 to 13 days after start of estrus is between 10 μg and 150 μg.

12. The method of claim 8 wherein said bFSH analog is a recombinant polypeptide.

13. The method of claim 8 wherein only a single dose of the bFSH analog is administered to each ungulate in a single estrus cycle.

14. The method of claim 8 further comprising administering at least one injection of prostaglandin to said one or more ungulates.

15. A method of increasing embryo production in one or more ungulates comprising administering between 1 μg and 0.2 mg of a bFSH analog to said one or more ungulates between 7 to 13 days after start of estrus and inseminating said ungulates 4 to 6 days after administration of said recombinant bFSH analog, wherein said bFSH analog comprises an amino acid sequence having at least 95% homology with SEQ ID NO: 10, wherein said ungulates are selected from the group consisting of bovine, equine, sheep and swine, wherein luteinizing hormone is not administered to said ungulates, and wherein administration of said bFSH analog increases the number of embryos produced by said one or more ungulates.

16. The method of claim 15 wherein said ungulates are bovine.

17. The method of claim 15 wherein the amount of said bFSH administered between 7 to 13 days after start of estrus is between 10 μg and 150 μg.

18. The method of claim 15 wherein said bFSH analog is a recombinant polypeptide.

19. The method of claim 15 wherein only a single dose of the bFSH analog is administered to each ungulate in a single estrus cycle.

20. The method of claim 15 further comprising administering at least one injection of prostaglandin to said one or more ungulates.

* * * * *

SEQUENCE LISTING

<160> NUMBER OF SEQ ID NOS: 11

<210> SEQ ID NO 1
<211> LENGTH: 96
<212> TYPE: PRT
<213> ORGANISM: Bos taurus

<400> SEQUENCE: 1

```
Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95
```

<210> SEQ ID NO 2
<211> LENGTH: 129
<212> TYPE: PRT
<213> ORGANISM: Bos taurus

<400> SEQUENCE: 2

```
Met Lys Ser Val Gln Phe Cys Phe Leu Phe Cys Cys Trp Arg Ala Ile
1               5                   10                  15

Cys Cys Arg Ser Cys Glu Leu Thr Asn Ile Thr Ile Thr Val Glu Lys
            20                  25                  30

Glu Glu Cys Gly Phe Cys Ile Ser Ile Asn Thr Thr Trp Cys Ala Gly
        35                  40                  45

Tyr Cys Tyr Thr Arg Asp Leu Val Tyr Arg Asp Pro Ala Arg Pro Asn
    50                  55                  60

Ile Gln Lys Thr Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Glu Cys His Cys Ser Lys Cys Asp Ser Asp Ser Thr Asp Cys
                100                 105                 110
```

Thr Val Arg Gly Leu Gly Pro Ser Tyr Cys Ser Phe Arg Glu Ile Lys
        115                 120                 125

Glu

<210> SEQ ID NO 3
<211> LENGTH: 28
<212> TYPE: PRT
<213> ORGANISM: Homo sapiens

<400> SEQUENCE: 3

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
gtgcatagga tgaagtctgt cc                                            22

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
ggcgcgttat tctttgattt ccc                                           23

<210> SEQ ID NO 6
<211> LENGTH: 27
<212> TYPE: DNA
<213> ORGANISM: Artificial
<220> FEATURE:
<223> OTHER INFORMATION: Primer

<400> SEQUENCE: 6
gccgaaagct tattatgaag tctgtcc                                       27

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
gaggaagagg attctttgat ttccc                                         25

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
gggaaatcaa agaatcctct tcctc                                         25

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
cgtgctggat ccttattagg atttgtg                                    27

<210> SEQ ID NO 10
<211> LENGTH: 253
<212> TYPE: PRT
<213> ORGANISM: Artificial
<220> FEATURE:
<223> OTHER INFORMATION: Synthetic Protein

<400> SEQUENCE: 10

Met Lys Ser Val Gln Phe Cys Phe Leu Phe Cys Cys Trp Arg Ala Ile
1               5                   10                  15

Cys Cys Arg Ser Cys Glu Leu Thr Asn Ile Thr Ile Thr Val Glu Lys
            20                  25                  30

Glu Glu Cys Gly Phe Cys Ile Ser Ile Asn Thr Thr Trp Cys Ala Gly
        35                  40                  45

Tyr Cys Tyr Thr Arg Asp Leu Val Tyr Arg Asp Pro Ala Arg Pro Asn
    50                  55                  60

Ile Gln Lys Thr Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Glu Cys His Cys Ser Lys Cys Asp Ser Asp Ser Thr Asp Cys
            100                 105                 110

Thr Val Arg Gly Leu Gly Pro Ser Tyr Cys Ser Phe Arg Glu Ile Lys
        115                 120                 125

Glu Ser Ser Ser Lys Ala Pro Pro Ser Leu Pro Ser Pro Ser
    130                 135                 140

Arg Leu Pro Gly Pro Ser Asp Thr Pro Ile Leu Pro Gln Phe Pro Asp
145                 150                 155                 160

Gly Glu Phe Thr Met Gln Gly Cys Pro Glu Cys Lys Leu Lys Glu Asn
                165                 170                 175

Lys Tyr Phe Ser Lys Pro Asp Ala Pro Ile Tyr Gln Cys Met Gly Cys
            180                 185                 190

Cys Phe Ser Arg Ala Tyr Pro Thr Pro Ala Arg Ser Lys Lys Thr Met
        195                 200                 205

Leu Val Pro Lys Asn Ile Thr Ser Glu Ala Thr Cys Cys Val Ala Lys
    210                 215                 220

Ala Phe Thr Lys Ala Thr Val Met Gly Asn Val Arg Val Glu Asn His
225                 230                 235                 240

Thr Glu Cys His Cys Ser Thr Cys Tyr Tyr His Lys Ser
                245                 250

<210> SEQ ID NO 11
<211> LENGTH: 762
<212> TYPE: DNA
<213> ORGANISM: Artificial
<220> FEATURE:
<223> OTHER INFORMATION: cDNA for synthetic protein

<400> SEQUENCE: 11

-continued

```
atgaagtctg tccagttctg tttccttttc tgttgctgga gagcaatctg ctgcagaagc    60
tgcgagctga ccaacatcac catcacggtg gagaaagagg aatgtggctt ctgcataagc   120
atcaacacca cgtggtgtgc aggctactgc tacacccggg acttggtgta cagggaccca   180
gcaaggccca atatccagaa aacgtgtacc ttcaaggagc tggtctacga dacggtgaaa   240
gtgcctggct gtgctcacca tgcagactcc ctgtacacgt acccagtagc cactgaatgt   300
cactgcagca agtgcgacag cgacagcact gactgcaccg tgcgaggcct ggggcccagc   360
tactgctcct tcagggaaat caaagaatcc tcttcctcaa aggcccctcc cccgagcctt   420
ccaagtccat cccgactccc ggggccctcg gacacccccga tcctcccaca atttcctgat   480
ggagagttta caatgcaggg ctgtcctgaa tgcaagctaa aagaaaacaa atacttctcc   540
aagccagatg ctccaatcta tcagtgcatg gggtgctgct tctccagggc atacccccact   600 ccagcgaggt ctaagaagac aatgttggtc cccaagaaca tcacctcgga agctacatgc   660
tgtgtggcca aagcatttac caaggccaca gtgatgggaa atgtcagagt ggagaaccac   720
accgagtgcc actgcagcac ttgttattat cacaaatcct ga                      762
```